US005823962A

United States Patent [19]

Schaetzle et al.

[11] Patent Number: 5,823,962

[45] Date of Patent: Oct. 20, 1998

[54] ULTRASOUND TRANSDUCER FOR DIAGNOSTIC AND THERAPEUTIC USE

[75] Inventors: Ulrich Schaetzle, Roettenbach, Germany; Todor Sheljaskov, Linz, Austria; Reinhard Lerch, Heroldsberg, Germany

[73] Assignee: Siemens Aktiengesellschaft, Munich, Germany

[21] Appl. No.: 921,827

[22] Filed: Sep. 2, 1997

[30] Foreign Application Priority Data

Sep. 2, 1996 [DE] Germany ........................ 196 35 593.1

[51] Int. Cl.[6] ...................................................... A61B 17/22

[52] U.S. Cl. .............................. 600/439; 600/459; 601/2; 601/3; 310/366

[58] Field of Search ............................ 601/2–4; 600/439, 600/443, 447, 459; 310/311, 322, 334, 337, 365–366

[56] References Cited

U.S. PATENT DOCUMENTS 5,163,436 11/1992 Saitoh et al. .
5,526,815 6/1996 Granz et al. ............................ 600/439

FOREIGN PATENT DOCUMENTS 0 451 984 5/1995 European Pat. Off. .

OTHER PUBLICATIONS

"High–Intensity Focused Ultrasound Experimentation on Human Benign Prostatic Hypertrophy," Gelet et al., Eur. Urol., vol. 23 (Suppl. 1), 1993, pp. 44–47.

"Intense Focused Ultrasound in Medicine," Fry, Eur. Urol., vol. 23 (Suppl. 1), 1993, pp. 2–7.

"A Dual Frequency Ultrasonic Probe for Medical Applications," Saitoh et al., IEEE Trans. on Ultrasonics, Ferroelectrics and Frequency Control, vol. 42, No. 2, Mar. 1991, pp. 294–300.

"A Novel Acoustic Design for Dual Frequency Transducers Resulting in Separate Bandpass for Color Flow Mapping (CPM)," de Fraguler et al., Proc. IEEE, 1990 Ultrasonics Symposium, pp. 799–803.

"Improving the Characteristics of a Transducer Using Multiple Piezoelectric Layers," Hossack et al., IEEE Trans. on Ultrasonics, Ferroelectrics and Frequency Control, vol. 40, No. 2, Mar. 1993, pp. 131–139.

"Multiple Layer Transducers for Broadband Applications," Hossack et al., Proc. IEEE Ultrasonics Symposium, 1991, pp. 605–611.

*Primary Examiner*—Ruth S. Smith
*Attorney, Agent, or Firm*—Hill & Simpson

[57] ABSTRACT

An ultrasound transducer for diagnostic and therapeutic generates ultrasound waves of different wavelengths in diagnostics mode or therapy mode. The ultrasound transducer has an n×λ/4 matching layer for a propagation medium adjoining the ultrasound transducer, and a piezoelectric ultrasound transducer element with a first electrode located between the matching layer and the ultrasound transducer element, a second electrode attached at the opposite side of the ultrasound transducer element, and a third electrode that divides the ultrasound transducer element into two regions. Ultrasound waves can be generated for the diagnostics mode and for the therapy mode dependent on the division of the ultrasound transducer element. The n×λ/4 matching layer is effective for the wavelength of the ultrasound waves in diagnostics mode as well as in therapy mode.

20 Claims, 6 Drawing Sheets

ULTRASOUND TRANSDUCER FOR DIAGNOSTIC AND THERAPEUTIC USE

BACKGROUND OF THE INVENTION

1. Field of the Invention

The present invention is directed to an ultrasound transducer of the type having a matching layer for a propagation medium for ultrasound waves adjoining the ultrasound transducer and an ultrasound transducer element with a first electrode located between the matching layer and the ultrasound transducer element and a second electrode attached at that side of the ultrasound transducer element lying opposite the matching layer.

2. Description of the Prior Art

Applications of ultrasound in medicine, for example for therapy of benign prostate hyperplasia, usually employ focused ultrasound waves that are generated by sources known as HIFU sources (high-intensity focused ultrasound) that charge a pathological tissue to be treated with focused ultrasound waves and thus heat the tissue. Insofar as the resulting temperature lies below 45° C., the cell metabolism is disturbed with the result that, given tumors, a retardation of the growth or even a reversal of the tumor occurs. This type of treatment is known as local hyperthermia. When temperatures beyond 90° C. are reached, the cell protein coagulates resulting in necrotization of the tissue. This latter type of treatment is referred to as thermotherapy. The therapeutic ultrasound waves are emitted by the ultrasound source as continuous sound or as a sequence of ultrasound bursts. Such ultrasound sources are usually combined with a suitable diagnostic, imaging system, allowing a physician treating pathological tissue modifications in the body of a patient to be provided with the opportunity of exactly localizing the treatment area in the body of the patient and to observe the process of the therapy with focused ultrasound waves in real time for monitoring and correspondingly controlling it. In addition to an ultrasound transducer or an array of ultrasound transducers for therapy, ultrasound applicators often also include an ultrasound transducer or an array of ultrasound transducers for diagnostics that is usually in a spatially separate (from the therapeutic array) component of the ultrasound applicator and is also usually operated separately from the therapeutic array.

Currently employed sonographic methods for diagnosis, i.e. imaging, of the treatment area include, for example, the sector scan with an ultrasound transducer rotating relative to the therapeutic ultrasound transducer (see "High-Intensity Focused Ultrasound Experimentation On Human Benign Prostatic Hypertrophy", European Urology, vol. 23, Suppl. 1, 1993, ISSN 0302-2838, by A. Gelet, J. Y. Chapelon, J. Margonari, Y. Theillère, F. Gorry, R. Souchon) or the linear scan wherein the diagnosis transducer is displaced over the treatment area. As used herein, therefore, a scan means, a linear or sector-shaped scanning with ultrasound arrays.

The employment of the above-described ultrasound applicators that have two separate ultrasound systems for therapy and for diagnostics, however, involves risks. First, so-called misdirections can occur, i.e. the treatment zone on which the therapeutic ultrasound waves act is often not exactly located in the diagnostics region since, due to the different incident angles of the therapeutic and diagnostic ultrasound waves into the body tissue, the ultrasound waves traverse different paths in the body tissue and a different diffraction of the ultrasound waves occurs on the different paths through the body tissue. Second, there is the risk of an imprecise alignment or an incorrect alignment of the two ultrasound sources relative to one another. In all of these instances, thus, focused ultrasound waves in a therapy mode can miss the therapy target and damage healthy body tissue. The complicated alignment of the two ultrasound sources relative to one another as well as the mechanical scan device required for the diagnostics transducer also make the manufacture of such ultrasound applicators more difficult and more expensive.

New development tendencies therefore aim at the development of ultrasound applicators that are suitable both for receiving and generating ultrasound waves in different frequency ranges that can thus be utilized in medicine for diagnostics and therapy. In ultrasound technology, moreover, there is an increasing reliance on the use of linear phased arrays of ultrasound transducers, for example in the treatment of benign prostate hyperplasia, whereby a pivoted wave front can be generated by a chronologically offset electrical excitation of the linearly arranged array elements, so that an electronic focusing of the generated ultrasound waves in a plane is possible.

Such a linear phased array of this type is shown, for example, in FIG. 1, five ultrasound transducers thereof being shown. Each ultrasound transducer $\mathbf{1}_1$ through $\mathbf{1}_5$ of the ultrasound array has an ultrasound transducer element $\mathbf{2}_1$ through $\mathbf{2}_5$ formed of a piezo ceramic and a $\lambda/4$ matching layer $\mathbf{3}_1$ through $\mathbf{3}_5$, formed, for example, from an epoxy resin laced with copper particles, at an acoustic propagation medium 4 (water in the present case) adjoining the ultrasound transducers $\mathbf{1}_1$ through $\mathbf{1}_5$. The ultrasound transducer elements $\mathbf{2}_1$ through $\mathbf{2}_5$ are respectively provided with two electrodes, namely an electrode $\mathbf{5}_1$ through $\mathbf{5}_5$ located between the ultrasound transducer element and the matching layer that is connected to ground and an electrode $\mathbf{6}_1$ through $\mathbf{6}_5$ attached at the side lying opposite the matching layer and to which the voltage U directed to ground is respectively applied for control. The ultrasound array of the ultrasound transducers $\mathbf{1}_1$ through $\mathbf{1}_5$ is also protected by a foil 7 disposed between the propagation medium 4 and the ultrasound transducers $\mathbf{1}_1$ through $\mathbf{1}_5$. The foil 7 protects against penetration of the propagation medium into the interspaces between the ultrasound transducers $\mathbf{1}_1$ through $\mathbf{1}_5$.

For example, German OS 43 02 538 discloses a linear phased array of ultrasound transducers of a therapy apparatus for locating and treating a zone situated in the body of a living subject. The electroacoustic transducer is optionally employable in therapy mode or in locating mode.

In the development of ultrasound applicators that are suitable both for therapy and for diagnostics, however, technical problems arise because ultrasound transducers or arrays of ultrasound transducers must exhibit different acoustic properties for the diagnostic mode and the therapy mode. For example, a high resonance quality and a high efficiency of the ultrasound transducer, of the array element of the ultrasound transducer, are required in a therapy mode of an ultrasound applicator, whereas a high bandwidth of the ultrasound transducer, or of the array elements of the ultrasound transducer, is needed in diagnostics, i.e. in imaging. Another technical problem lies in generating different ultrasound frequencies with a single ultrasound applicator for therapy mode and diagnostic mode. The ultrasound frequencies currently employed for therapy mode lie largely in the frequency band between 0.25 and 4 MHZ (see "Intense Focused Ultrasound in Medicine", European Urology, Vol. 23, Suppl. 1, 1993, ISSN 0302-2838, by F. Fry), whereas frequencies above 5 MHZ are employed for sonography.

In the current state of the art, two groups of basic solutions are favored for ultrasound applicators that can be utilized in diagnostics mode and in therapy mode. One involves structures of ultrasound transducer elements that are, for example, formed by a two-layer embodiment of piezoelectric material, and thus exhibit two pronounced thickness resonances and essentially oscillate with the frequency of one of the two thickness resonances on the basis of designational electrical excitation in one of the two desired oscillatory modes (see "A Dual Frequency Ultrasonic Probe For Medical Applications", IEEE Trans. On Ultrasonics, Ferroelectrics, and Frequency Control, Vol. 42, No. 2, 1995, by S. Saitoh, M. Izumi, Y Mine, as well as "A novel acoustic design for dual frequency transducers resulting in separate bandpass for Color Flow Mapping (CFM)", Proc. IEEE Ultrasonics Symposium, 1990, S. Fraguier, J. Gelly, L. Wolnerman, O. Lannuzel). The other group employs various embodiments of ultrasound transducers in the form known as stacked transducers, whose layers of piezo ceramic must be repolarized for transmitting or receiving ultrasound waves at different frequencies (see EP 0 451 984 B1) or must be independently driven (see "Improving the Characteristics of a Transducer Using Multiple Piezoelectric Layers", IEEE Trans. on Ultrasonics, Ferroelectrics, and Frequency Control, Vol. 40, No. 2, 1993, by J. Hossack, B. Auld, as well as "Multiple Layer Transducers For Broadband Applications", Proc. IEEE Ultrasonics Symposium, 1991, by J. Hossack, B. Auld).

The problem of optimum acoustic matching of the ultrasound transducer element of the ultrasound transducer to the propagation medium for ultrasound waves adjoining the ultrasound transducer for the frequency ranges employed in the therapy mode as well as in the diagnostics mode is still unsolved in the art. The same is true as to the problem of achieving an optimally high resonant quality of the ultrasound transducers in therapy and an optimally large attenuation of the ultrasound waves in diagnostics.

SUMMARY OF THE INVENTION

An object of the present invention is to provide an ultrasound transducer which can be optionally utilized for ultrasound therapy or diagnostics and which is acoustically matched in each mode to a propagation medium adjoining the ultrasound transducer.

This object is inventively achieved in an ultrasound transducer for diagnostic and therapeutic employment that optionally generates ultrasound waves with different wavelengths in diagnostics mode or therapy mode, wherein the wavelength of the ultrasound waves in diagnostics mode is less than the wavelength of the ultrasound waves in therapy mode, having an $n \times \lambda/4$ matching layer for a propagation medium for ultrasound waves adjoining the ultrasound transducer, whereby n is an odd number, and a piezoelectric ultrasound transducer element having a first electrode located between the matching layer and the ultrasound transducer element, a second electrode applied on that side of the ultrasound transducer element lying opposite the matching layer, and a third electrode that divides the ultrasound transducer element into a region neighboring the matching layer lying at one side of the third electrode and a region lying at the other side of the third electrode and that forms a common ground contact for the two regions. Ultrasound waves with different frequency can be generated for the diagnostics and therapy mode dependent on the division of the ultrasound transducer element, because different electrical control signals can be provided for the generation thereof at the two regions in diagnostics mode and therapy mode, and because the $n \times \lambda/4$ matching layer is made effective for the wavelength of the ultrasound waves in diagnostics mode as well as in therapy mode. As a result of the division of the ultrasound transducer element into two regions with the third electrode, thus, a separate, mutually independent electrical drive of the two regions of the ultrasound transducer element is optionally possible for a diagnostic and therapeutic use of the ultrasound transducer, allowing the frequencies of the generated acoustic ultrasound waves to be matched, on the one hand, to the requirements of the therapy mode and, on the other hand, to the requirements of the locating mode, while always maintaining the ultrasound transducer acoustically matched to the propagation medium adjoining the ultrasound transducer via the $n \times \lambda/4$ matching layer. This represents a considerable advantage over known transducers, since the acoustic matching of the ultrasound transducer to a propagation medium adjoining the ultrasound transducer, and which exhibits a characteristic impedance differing from the characteristic impedance of the ultrasound transducer, is of critical significance for achieving an optimally reflection-free transition of the sound energy from the ultrasound transducer into the propagation medium. This reflection-free transition is important so as to minimize the treatment time and for achieving the desired medical purpose with an optimally low dose of acoustic energy supplied to the patient, particularly in therapy mode.

In a preferred embodiment of the invention the third electrode divides the region of the ultrasound transducer element lying on one side of the third electrode neighboring the matching layer in a thickness ratio of 1:2 relative to the region of the ultrasound transducer element lying on the other side of the third electrode. In therapy mode of the ultrasound transducer, control signals, i.e. control voltages—preferably in the form of sinusoidal bursts—are then present across both regions of the ultrasound transducer element, whereby the control voltage adjacent at the region lying at the one side of the third electrode is essentially equal to −½ given substantially the same polarization of the two regions, and, given substantially opposite polarization of the two regions, is essentially equal to +½ of the control voltage $U_1$ across the region lying at the other side of the third electrode. A uniform electrical field within the ultrasound transducer element is generated in this way. In this case, the ultrasound transducer behaves like a thickness oscillator whose thickness is essentially equal to half the wavelength of its fundamental resonant frequency, and that essentially oscillates with the frequency of its thickness resonance and generates ultrasound waves suitable for therapy, i.e. ultrasound waves with frequencies between 0.25 and 4 MHZ dependent on the thickness of the ultrasound transducer element.

In a further version of the invention, the region lying at the other side of the third electrode of the ultrasound transducer in diagnostics mode is terminated with an electrical resistance matched to the corresponding impedance of the region of the ultrasound transducer element lying at the other side of the third electrode, so that ultrasound waves are more highly attenuated in this region of the ultrasound transducer element. As a result, the mechanical reverberation of the ultrasound transducer element after the deactivation of the electrical excitation pulse or control signal is reduced. Further, the bandwidth of the ultrasound transducer is increased as a result of this measure. Further, a control voltage is then present only across the region lying at the one side of the third electrode. Since the thickness of the region lying at the one side of the third electrode, which is driven with corresponding control voltages in diagnostics mode and that divides the ultrasound transducer in the ratio 1:2, amounts to one-third of the overall thickness of the ultrasound transducer element, the matching layer now is effectively a ¾λ matching layer with respect to the frequency of the thickness resonance of the region lying at the one side of the third electrode. As a result, the ultrasound transducer element is again acoustically matched to the propagation medium adjoining the ultrasound transducer. The region lying at the one side of the third electrode can thus be operated with control voltages, preferably in the form of sinusoidal bursts, having three times the frequency with respect to the control voltages employed in therapy mode.

According to a preferred embodiment of the invention, the region of the ultrasound transducer element lying at the one side of the third electrode, together with the matching layer, is divided into discrete oscillators independent of one another, that can be driven with control signals. Preferably this region is subdivided into three mutually independent discrete oscillators that can be driven with control voltages $U_2$, $U_3$ and $U_4$ via their respective first electrodes. Due to the division of the matching layer and of the region lying at the one side of the third electrode into a number of discrete oscillators, the width/thickness ratio of the region of the ultrasound transducer element lying at the one side of the third electrode (that is unfavorable for diagnostics mode) is improved, so that the frequency separation between transverse oscillation and thickness oscillation mode is increased and the risk of the an undesired excitation of a parasitic transverse oscillation mode, that can disturb the ultrasound field generated by a designationally excited oscillatory mode, is reduced. Another advantage of this subdivision is the clearly reduced spacing of the discrete oscillators from one another (element to element spacing). The creation of side lobes in the generated ultrasound field at the shorter wavelength of the ultrasound waves in diagnostics mode is thereby reduced in the propagation medium adjoining the ultrasound transducers.

Due to the division of the matching layer and the region lying at the one side of the third electrode into three or more discrete oscillators, individual control voltages can be applied at the discrete oscillators in therapy mode of the ultrasound transducer that, in the case of three discrete oscillators, are essentially $U_2=U_3=U_4=-\frac{1}{2} U_1$ given essentially identical polarization of the two regions and that are essentially $U_2=U_3=U_4=+\frac{1}{2} U_1$ given essentially opposite polarization of the two regions. As in the above-described case, a uniform electrical field in the ultrasound transducer element also occurs in this embodiment of the ultrasound transducer, so that the ultrasound transducer again behaves like a thickness oscillator that oscillates with the frequency of its thickness resonance. In diagnostics mode, the region lying at the other side of the third electrode is again terminated with an electrical resistance matched to the corresponding impedance, and control voltages $U_2$, $U_3$ and $U_4$ are applied only to the three individual oscillators.

In another version of the invention the ultrasound transducer elements at the side lying opposite the matching layer are terminated with air, resulting in the high power efficiency required for the therapy mode of the ultrasound transducer being achieved for the purpose of a short treatment time for the patient.

According to another embodiment of the invention, the ultrasound transducer element formed of a piezoceramic, for example, Vibrit 420, that is well-suited for therapy as well as for diagnostics mode of an ultrasound transducer because of its material parameters. The matching layer of the ultrasound transducer is formed of an epoxy resin laced with copper particles that, even in the form of a single matching layer, effects a comparatively good approximation of the acoustic impedance of the piezo-ceramic to the propagation medium adjoining the ultrasound transducer. In addition, the epoxy resin laced with copper particles exhibits a relatively low attenuation for ultrasound waves and can be easily cooled, this being a significant advantage within an ultrasound applicator.

In a further version of the invention the ultrasound transducer is formed of two elements of piezoceramic that are provided with contact surfaces and that have their contact surfaces lying against one another for forming the third electrode. In this way, the third electrode of the ultrasound transducer element can be realized in an especially simple way.

In another embodiment of the invention the ultrasound transducer is fashioned as a sintered member, with the third electrode being formed during the course of a sintering process. No fabrication steps going beyond the sintering process are thus required for the formation of the third electrode.

The division of the matching layer and of the region of the ultrasound transducer element lying at the one side of the third electrode ensues by sawing in one version of the invention, with a saw cut of such a depth being made until the third electrode is created. The sawing, moreover, preferably ensues in equidistant steps, so that all discrete oscillators of the ultrasound transducer element produced in this way have essentially the same width and the same spacing from one another.

In another preferred version of the invention the ultrasound transducer generates focused ultrasound waves, and the ultrasound transducer can also be fashioned in the form of an ultrasound array containing a plurality of ultrasound transducers. The ultrasound array can be operated as a linear array, i.e. with a linear arrangement of a plurality of ultrasound transducers, as a phased array, i.e. as an arrangement of a plurality of ultrasound transducers that generate electronically focused ultrasound waves on the basis of a chronologically delayed drive, or can be operated in combination as a linear phased array. In this case, it is easily possible in a known way to displace the action zone of the therapeutic acoustic waves by electronic control corresponding to the respective requirements in therapy mode, and to scan a subject to be treated with the diagnostic acoustic waves in locating mode in the manner required for producing a B-mode ultrasound image.

In another embodiment of the invention a foil, for example a Hostaphan seal foil having a thickness of approximately 20 $\mu$m, is present between the matching layer and the propagation medium, for preventing penetration of the propagation medium adjoining the ultrasound transducer or the array of ultrasound transducers into the interspaces between the ultrasound transducers and/or the discrete oscillators of the ultrasound transducers, so that no undesired electrical contacting of the three electrodes due to the propagation medium can occur. The foil is secured to the matching layer, preferably with a compound adhesive, for example Araldit.

DESCRIPTION OF THE PREFERRED EMBODIMENTS

Figure 2:
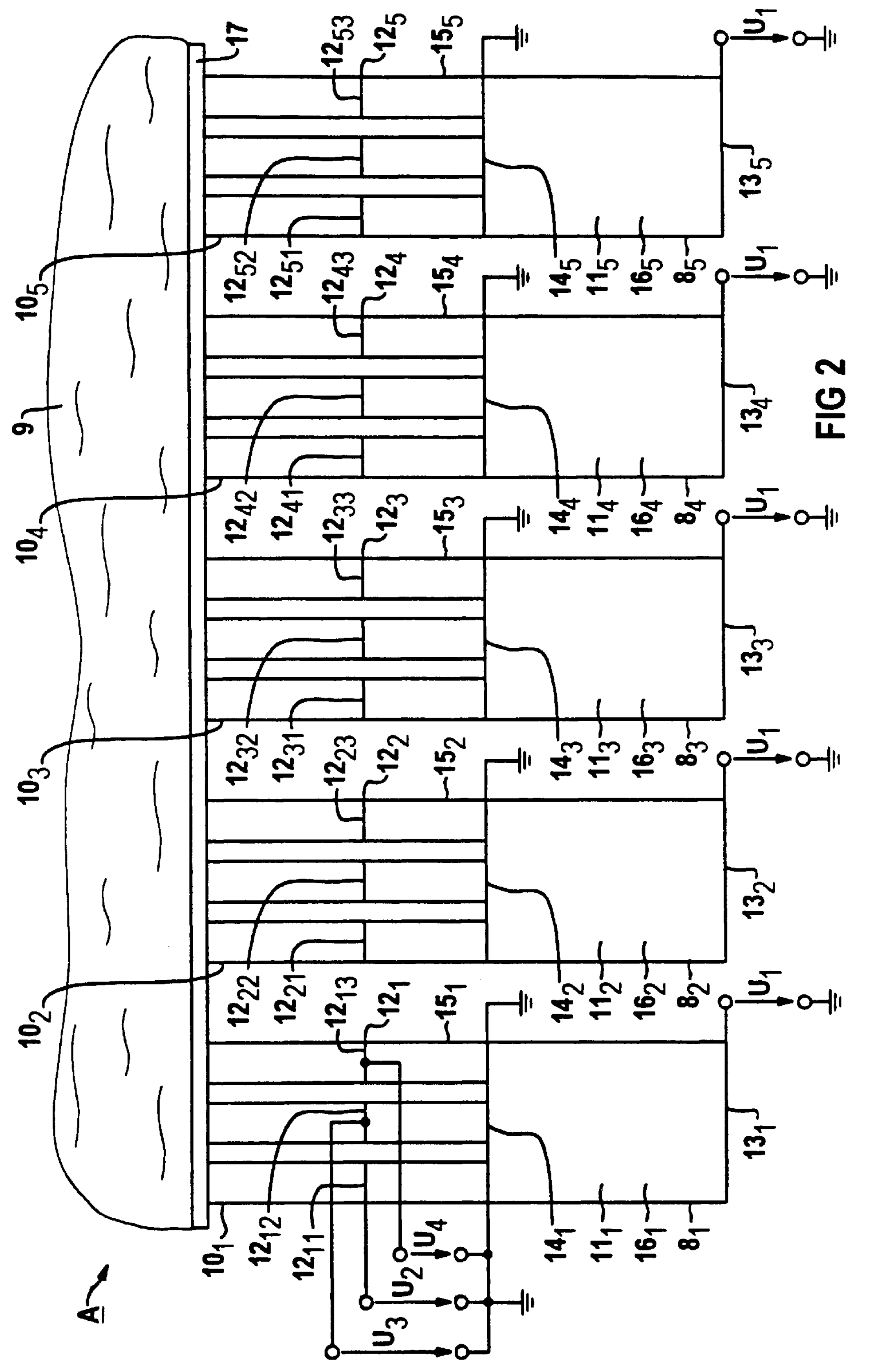
FIG. 2 is a schematic illustration of a linear phased array of inventive ultrasound transducers.

Of an ultrasound array A containing inventive ultrasound transducers, FIG. 2 shows five ultrasound transducers $\mathbf{8}_1$ through $\mathbf{8}_5$. Each of the illustrated, five ultrasound transducers $\mathbf{8}_1$ through $\mathbf{8}_5$ of the ultrasound array A has a λ/4 matching layer $\mathbf{10}_1$ through $\mathbf{10}_5$ that is formed of an epoxy resin laced with copper particles and that adjoins an acoustic propagation medium 9 (water in the present case), and an ultrasound transducer element $\mathbf{11}_1$ through $\mathbf{11}_5$ formed of a piezoceramic, for example Vibrit 420. Each of the five, illustrated ultrasound transducer elements $\mathbf{11}_1$ through $\mathbf{11}_5$ of the ultrasound array A is provided with three electrodes. First electrodes $\mathbf{12}_1$ through $\mathbf{12}_5$ are respectively situated between the matching layers $\mathbf{10}_1$ through $\mathbf{10}_5$ and the ultrasound transducers $\mathbf{11}_1$ through $\mathbf{11}_5$. Second electrodes $\mathbf{13}_1$ through $\mathbf{13}_5$ are respectively attached to that side of the ultrasound transducer elements $\mathbf{11}_1$ through $\mathbf{11}_5$ lying opposite the matching layers $\mathbf{10}_1$ through $\mathbf{10}_5$, and third electrodes $\mathbf{14}_1$ through $\mathbf{14}_5$ respectively divide the ultrasound transducer elements $\mathbf{11}_1$ through $\mathbf{11}_5$ into an upper regions $\mathbf{15}_1$ through $\mathbf{15}_5$ neighboring the matching layers $\mathbf{10}_1$ through $\mathbf{10}_5$ and lower regions $\mathbf{16}_1$ through $\mathbf{16}_5$. The division by the third electrodes $\mathbf{14}_1$ through $\mathbf{14}_5$ in the present case ensues in a thickness ratio of 1:2. Together with the λ/4 matching layers $\mathbf{10}_1$ through $\mathbf{10}_5$, each upper region $\mathbf{15}_1$ through $\mathbf{15}_5$ of the ultrasound transducer elements $\mathbf{11}_1$ through $\mathbf{11}_5$ is additionally divided into three discrete oscillators, so that each discrete oscillator—viewed in and of itself—has three first electrodes $\mathbf{12}_{m1}$ through $\mathbf{12}_{m3}$ with m=1–5. The first electrodes $\mathbf{12}_{11}$ through $\mathbf{12}_{53}$ of the discrete oscillators of the ultrasound transducers $\mathbf{8}_1$ through $\mathbf{8}_5$ as well as the second and third electrodes of the ultrasound transducers $\mathbf{8}_1$ through $\mathbf{8}_5$ can be electrically contacted independently of one another. For clarity in FIG. 2, moreover, the matching layers and the upper regions of the ultrasound transducer elements of the discrete oscillators of the ultrasound transducers $\mathbf{8}_1$ through $\mathbf{8}_5$ have not been provided with separate reference characters. When, for example, matching layers $\mathbf{10}_1$ through $\mathbf{10}_5$ are mentioned below, the matching layers of all discrete oscillators of the ultrasound transducers $\mathbf{8}_1$ through $\mathbf{8}_5$ are meant.

The division of the matching layers $\mathbf{10}_1$ through $\mathbf{10}_5$ and of the upper regions $\mathbf{15}_1$ through $\mathbf{15}_5$ of the ultrasound transducer elements $\mathbf{11}_1$ through $\mathbf{11}_5$, moreover, preferably but not necessarily ensues by sawing, with the width of the discrete oscillators and the spacing of the discrete oscillators from one another produced by the sum kerfs being essentially constant and the same for each of the ultrasound transducers $\mathbf{8}_1$ through $\mathbf{8}_5$. The width of a discrete oscillator usually amounts to approximately 50 through 100 μm, and the spacing of the discrete oscillators of each of the ultrasound transducers $\mathbf{8}_1$ through $\mathbf{8}_5$ from one another amounts to approximately 25 through 50 μm. The spacing of the ultrasound transducers $\mathbf{8}_1$ through $\mathbf{8}_5$ of the ultrasound array A amounts to approximately 50 through 100 μm (also see FIG. 4 with respect thereto).

The third electrodes $\mathbf{14}_1$ through $\mathbf{14}_5$ of the ultrasound transducers $\mathbf{8}_1$ through $\mathbf{8}_5$ of the ultrasound array A, moreover, form the shared ground contact of the upper regions $\mathbf{15}_1$ through $\mathbf{15}_5$ and lower regions $\mathbf{16}_1$ through $\mathbf{16}_5$ of the ultrasound transducer elements $\mathbf{11}_1$ through $\mathbf{11}_5$. The formation of such a third electrode $\mathbf{14}_1$ through $\mathbf{14}_5$ located between an upper and a lower region of an ultrasound transducer element can ensue before the division into discrete oscillators, for example by placing two ceramic layers provided with contact surfaces together, with the contact surfaces lying against one another forming the third electrode $\mathbf{14}_1$ through $\mathbf{14}_5$. Known techniques in sintering technology are available for forming the third electrodes $\mathbf{14}_1$ through $\mathbf{14}_5$ during the course of a sintering process.

A foil 17, for example a Hostaphan and seal foil having a thickness of approximately 20 μm, is glued onto the matching $\mathbf{10}_1$ through $\mathbf{10}_5$ of the discrete oscillators of the ultrasound transducers $\mathbf{8}_1$ through $\mathbf{8}_5$ forming the ultrasound array A with, for example, the compound adhesive Araldit. The foil 17 is thus located between the matching layers $\mathbf{10}_1$ through $\mathbf{10}_5$ of the discrete oscillators of the ultrasound transducers $\mathbf{8}_1$ through $\mathbf{8}_5$ and the acoustic propagation medium 9 and prevents penetration of acoustic propagation medium into the interspaces present between the discrete oscillators and the ultrasound transducers $\mathbf{8}_1$ through $\mathbf{8}_5$. It is thereby assured that no undesired electrical contactings between the first, second and third electrodes of the ultrasound transducers $\mathbf{8}_1$ through $\mathbf{8}_5$ can occur due to the acoustic propagation medium.

The ultrasound array A is operated as a linear phased array in therapy mode and in diagnostics mode and generates ultrasound waves that can be electronically focused in a plane. This operating mode of the ultrasound array A, however, is not mandatory.

In the locating mode, the ultrasound array A generates diagnostic acoustic waves in the form of short ultrasound pulses whose length amounts to a few half-cycles. In therapy mode, the ultrasound array A additionally generates focused, therapeutic acoustic ultrasound waves. These ultrasound waves can be continuous sound (CW) or pulses of continuous sound that is respectively briefly interrupted for emission of the diagnostic ultrasound waves, that are preferably focused.

In therapy mode, all regions of the ultrasound transducer $\mathbf{11}_1$ through $\mathbf{11}_5$—these include the lower regions $\mathbf{16}_1$ through $\mathbf{16}_5$ and the upper regions $\mathbf{15}_1$ through $\mathbf{15}_5$ divided into three discrete oscillators—are driven with control signals for generating therapeutic acoustic ultrasound waves, preferably in the form of sinusoidal bursts, whereby $U_2=U_3=U_4=-½\ U_1$ is selected since the polarization of the lower regions $\mathbf{16}_1$ through $\mathbf{16}_5$ and upper regions $\mathbf{15}_1$ through $\mathbf{15}_5$ is essentially the same in the present case. As can be seen from FIG. 2, the control signals or control voltages are applied at each ultrasound transducer $\mathbf{8}_1$ through $\mathbf{8}_5$. The lower regions of the ultrasound transducer elements $\mathbf{11}_1$ through $\mathbf{11}_5$ are respectively driven via the second electrode $\mathbf{13}_1$ through $\mathbf{13}_5$ with the control voltage $U_1$ relative to ground and each discrete oscillator of one of the ultrasound transducers $\mathbf{8}_1$ through $\mathbf{8}_5$ is driven via its first electrode $\mathbf{12}_{11}$ through $\mathbf{12}_{53}$ with a control voltage $U_2$, $U_3$ or $U_4$ relative to ground. For clarity the electrical contacting of the first electrodes of the discrete oscillators (i.e. of the ultrasound transducer elements $\mathbf{11}_1$ through $\mathbf{11}_5$) is only shown by way of example in FIG. 2 with reference to the ultrasound transducer $\mathbf{11}_1$. The above-recited relationship between the control voltages $U_1$ $U_2$, $U_3$ and $U_4$ must be adhered to in therapy mode in the drive of the ultrasound transducer elements $11_1$ through $11_5$ in order to generate a uniform electrical field in the ultrasound transducer elements $11_1$ through $11_5$. Each of the ultrasound transducers $8_1$ through $8_5$ of the ultrasound array A then behaves like a thickness oscillator that essentially oscillates with the frequency of its thickness resonance and has a transient response that is comparable to that of the ultrasound transducers $1_1$ through $1_5$ of the ultrasound array of FIG. 1. The ultrasound transducers $8_1$ through $8_5$ are respectively acoustically matched to the propagation medium for ultrasound waves 9 via the λ/4 matching layers $10_1$ through $10_5$ of the discrete oscillators, whereby the thicknesses of λ/4 matching layers $10_1$ through $10_5$ are usually adapted to the operating frequencies of 1 through 3 MHZ for therapy mode and amount to approximately 200 through 600 μm. The piezoceramic, moreover, exhibits an overall thickness of approximately 400 through 1200 μm, whereby approximately ⅔ of the overall thickness is occupied by the lower regions $16_1$ through $16_5$ and approximately ⅓ is occupied by the upper regions $15_1$ through $15_5$ of the piezoceramic (i.e. of the ultrasound transducer elements $11_1$ through $11_5$). The ultrasound transducers $8_1$ through $8_5$, moreover, are terminated with air at the sides of the ultrasound transducer elements $11_1$ through $11_5$ lying opposite the matching layers $10_1$ through $10_5$, the high power efficiency of each and every ultrasound transducer $8_1$ through $8_5$ required for therapy mode thus being achieved.

Figure 6:
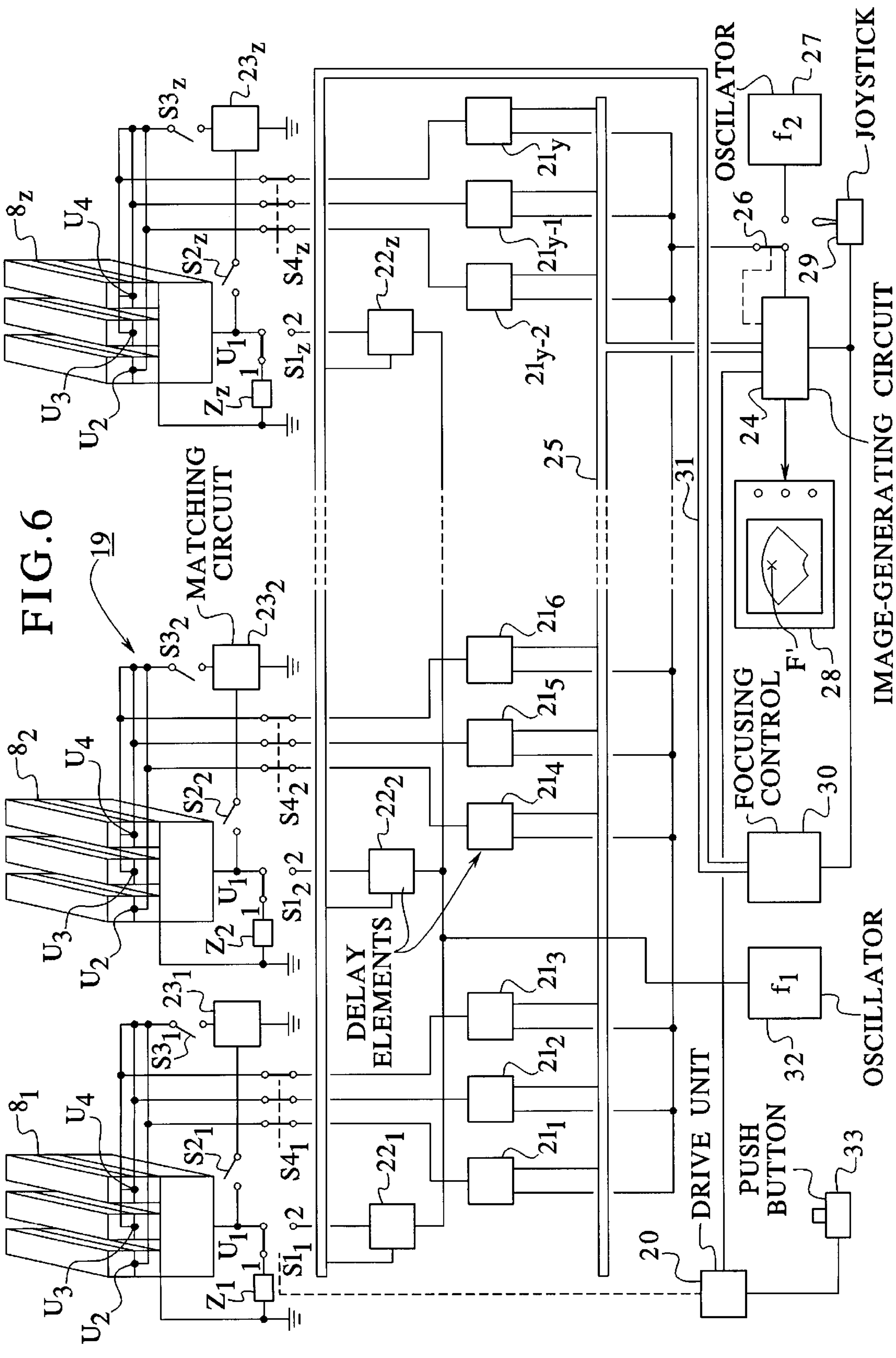
FIG. 6 is a block circuit diagram of a drive circuit for the linear phased array of inventive ultrasound transducers according to FIG. 3.

In diagnostics mode of the ultrasound array A, each lower region $16_1$ through $16_5$ of each ultrasound transducer element $11_1$ through $11_5$ is terminated with an electrical resistance matched to the corresponding impedance of the lower region $16_1$ through $16_5$ (see FIG. 6). In this way, ultrasound waves are more highly attenuated in the lower regions $16_1$ through $16_5$ of the ultrasound transducer elements $11_1$ through $11_5$. As a result, the mechanical reverberation after the deactivation of the electrical excitation pulse or control signal is reduced. Moreover, the bandwidth of the ultrasound array A is thereby enhanced for achieving a good imaging compared to the original array according to FIG. 1. In this operating instance of the ultrasound array A, only the three discrete oscillators lying above the third electrode in each ultrasound transducer $8_1$ through $8_5$ are respectively driven with control voltages $U_2$, $U_3$, and $U_4$. Since the thickness of the upper regions $15_1$ through $15_5$ of the ultrasound transducer elements $11_1$ through $11_5$ amounts to approximately ⅓ of the overall thickness of the piezoceramic ultrasound transducer elements $11_1$ through $11_5$, which lies between 400 and 1200 μm, the matching layer now effectively functions as a ¾ λ matching layer with respect to the thickness resonant frequency of the ultrasound transducers $8_1$ through $8_5$ in diagnostics mode. Thus the ultrasound transducer elements $11_1$ through $11_5$ are again acoustically matched to the propagation medium 9. The ultrasound transducer elements $11_1$ through $11_5$, (specifically the three discrete oscillators of each of the ultrasound transducers $11_1$ through $11_5$,) thus can be operated in diagnostics mode with three times the frequency, i.e. approximately 3–9 MHZ, compared to the sinusoidal bursts in therapy mode.

As a result of the division of the upper regions $15_1$ through $15_5$ of the ultrasound transducer elements $11_1$ through $11_5$ together with the matching layers $10_1$ through $10_5$ into three discrete oscillators independent of one another, moreover, the width-to-thickness ratio of the ultrasound transducer elements $11_1$ through $11_5$—which is otherwise unbeneficial—is taken into consideration in this range during diagnostics mode. This leads to a greater frequency separation between the transverse oscillation mode and the thickness oscillation mode; as a result the risk of an undesired excitation of a transverse oscillation mode is reduced. Undesired excitation of a transverse oscillation mode has the possibility of disturbing an ultrasound field generated designationally by thickness oscillations of the upper regions $15_1$ through $15_5$ of the ultrasound transducer elements $11_1$ through $11_5$. A further advantage of this division is the significantly smaller spacing of the antenna elements of the ultrasound array A, specifically of the discrete oscillators from one another (the term antenna elements being employed by analogy to communications or radio-frequency technology and refers to a device that can emit and receive electromagnetic waves). This minimizes the creation of side lobes at the shorter wavelength of the ultrasound waves in diagnostic mode in the propagation medium 9. Moreover, the division of the upper regions $15_1$ through $15_5$ of the ultrasound transducer elements $11_1$ through $11_5$ and of the matching layers $10_1$ through $10_5$ need not necessarily produce three discrete oscillators; other subdivisions are also possible.

Further, of course, it is possible to operate the inventive ultrasound transducer or the array of inventive ultrasound transducers in therapy mode and diagnostics mode with operating frequencies other than those cited. The thicknesses of the ultrasound transducer elements, their division, and the thickness of the n×λ/4 matching layers are adapted to the corresponding operating frequencies.

Figure 3:
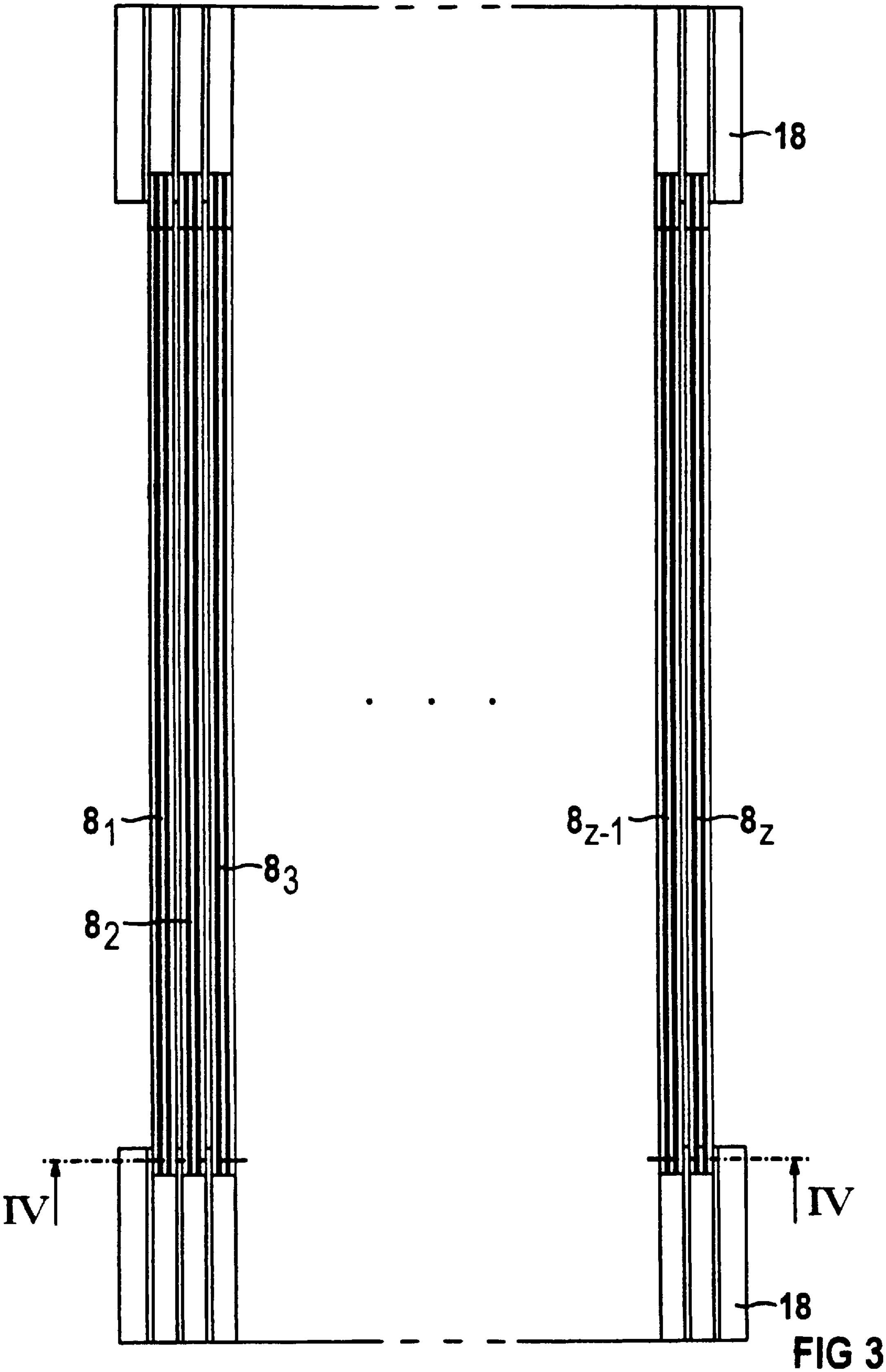
FIG. 3 is a plan view onto a linear phased array of inventive ultrasound transducers.
Figure 4:
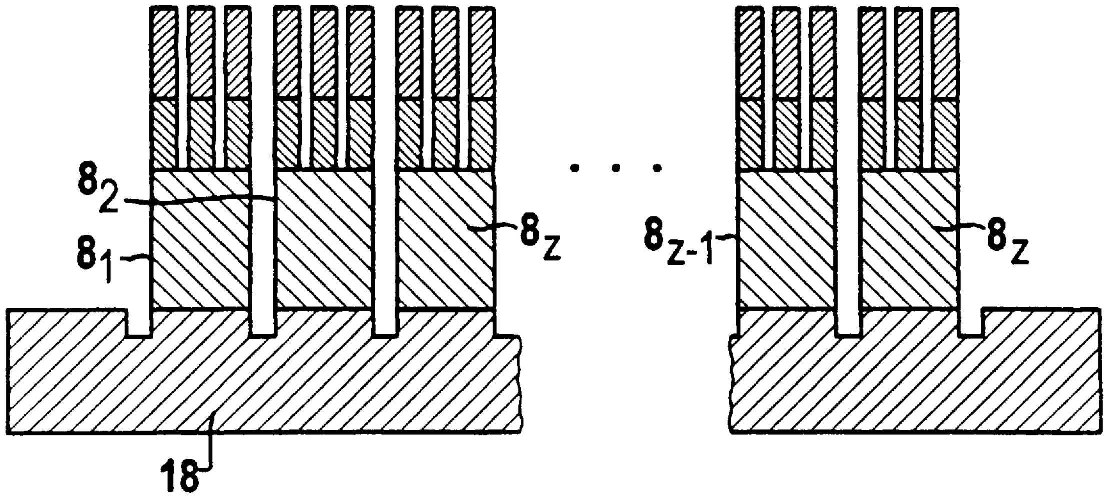
FIG. 4 is a sectional view along line IV—IV of FIG. 3.
Figure 5:
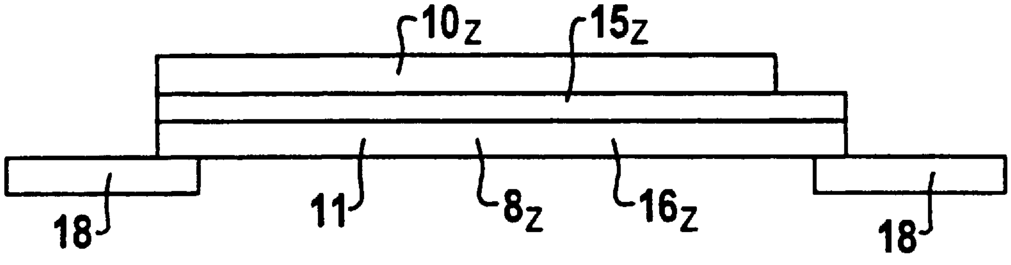
FIG. 5 is a side view of the array of inventive ultrasound transducer of FIG. 3.

In practice, moreover, the ultrasound array A contains a total of, for example, 128 or 256 ultrasound transducers. FIG. 3 shows a plan view of a corresponding ultrasound array A having z ultrasound transducers, with the foil 17 and the propagation medium 9 being omitted for clarity in FIG. 3. It can be seen in FIG. 3 that the ultrasound transducers $8_1$ through $8_z$ are secured to a frame 18 so that they are terminated at the rear by air in order, as already mentioned, to achieve a high power efficiency in therapy mode. FIG. 4 shows the section IV—IV from FIG. 3 in a presentation of the ultrasound array A comparable to FIG. 2. FIG. 5 shows a side view of the ultrasound array A.

The drive of the ultrasound transducers $8_1$ through $8_z$ is described below with reference to the block circuit diagram in FIG. 6 in which the ultrasound transducers $8_1$, $8_2$ and $8_z$ are shown by way of example. Via six different signal lines that are components of a connecting cable (not shown in FIG. 6), the transducers $8_1$ through $8_2$ are respectively connected to switches $S1_1$ through $S1_z$, $S2_1$ through $S2_z$, $S3_1$ through $S3_z$ and to a switch group $S4_1$ through $S4_z$ actually composed of three respective switches that, however, shall be treated as a single switch below. The switches $S1_1$ through $S4_z$ are components of control and image-generating electronics generally referenced 19. The switches $S1_1$ through $S4_z$, which are preferably electronic switches, are actuated by a drive unit 20. The switch positions in the two operating modes of the ultrasound array A shall be discussed in greater detail. The actuation of the switches $S1_1$ through $S4_z$ by the drive unit 20, moreover, is only schematically indicated by a broken line.

When the switches $S1_1$ through $S4_z$ assume their switch position shown in FIG. 6—which corresponds to the locating mode—, the switches $S1_1$ through $S1_z$ are in the switch position 1, the switches $S2_1$ through $S2_z$ and $S3_1$ through $S3_z$ are opened and the switches $S4_1$ through $S4_z$ are closed. In this operating condition of the ultrasound array A, the lower regions $16_1$ through $16_z$ of the ultrasound transducer elements $11_1$ through $11_z$ are terminated via electrical resistors $Z_1$ through $Z_z$ matched to the corresponding impedances of the lower regions $16_1$ through $16_z$. The values of resistance of the resistors $Z_1$ through $Z_z$ are substantially the same but can deviate slightly from one another due to slightly different impedance values of the lower regions $\mathbf{16}_1$ through $\mathbf{16}_z$ of the ultrasound transducer elements $\mathbf{11}_1$ through $\mathbf{11}_z$. Further, each discrete oscillator of each ultrasound transducer $\mathbf{8}_1$ through $\mathbf{8}_z$ is connected to a corresponding delay element $\mathbf{21}_1$ through $\mathbf{21}_y$ via a respective signal line and a respective switch of the switch groups $S4_1$ through $S4_z$.

When by contrast, the switches $S1_1$ through $S1_z$ are in switch position 2, the switches $S2_1$ through $S2_z$ and $S3_1$ through $S3_z$ are closed and the switches $S4_1$ through $S4_z$ are opened—as corresponds to therapy mode—, the lower regions $\mathbf{16}_1$ through $\mathbf{16}_z$ are the ultrasound transducer elements $\mathbf{11}_1$ through $\mathbf{11}_z$ are connected to delay elements $\mathbf{22}_1$ through $\mathbf{22}_z$. The lower regions $\mathbf{16}_1$ through $\mathbf{16}_z$ of the ultrasound transducer elements $\mathbf{11}_1$ through $\mathbf{11}_z$ are then driven via the delay elements $\mathbf{22}_1$ through $\mathbf{22}_z$ with control voltages $U_1$ relative to ground, preferably in the form of sinusoidal bursts. These sinusoidal bursts are also supplied to the discrete oscillators via matching circuits $\mathbf{23}_1$ through $\mathbf{23}_z$, whereby the matching circuits $\mathbf{23}_1$ through $\mathbf{23}_z$ cause $U_2=U_3=U_4=-½\ U_1$ to be substantially satisfied for the same polarization of the upper regions $\mathbf{15}_1$ through $\mathbf{15}_z$ and lower regions $\mathbf{16}_1$ through $\mathbf{16}_z$ of the ultrasound transducer elements $\mathbf{11}_1$ through $\mathbf{11}_z$.

The delay times of the delay elements $\mathbf{21}_1$ through $\mathbf{21}_y$ are individually set by an image-generating circuit 24 via a line bust 25. The setting of the delay times ensues such that a sector-shaped body slice of the subject to be treated is scanned when the delay elements $\mathbf{21}_1$ through $\mathbf{21}_y$ are connected in alternation to an oscillator 27, or to the image-generating circuit 24, by the switch 26 actuated by the image-generating circuit 24. The corresponding ultrasound image is displayed on a monitor 28 connected to the image-generating circuit 24. When the discrete oscillators of the ultrasound transducers $\mathbf{8}_1$ through $\mathbf{8}_z$ are connected to the oscillator 27 via the delay elements $\mathbf{21}_1$ through $\mathbf{21}_y$ and the switch 26, this drives them to emit an ultrasound pulse.

Immediately thereafter, the image-generating circuit 24 changes the switch position of the switch 26 such that the signals corresponding to the reflected parts of the ultrasound pulses received with the ultrasound transducers $\mathbf{8}_1$ through $\mathbf{8}_z$ arrive at the image-generating circuit 24 via the delay elements $\mathbf{21}_1$ through $\mathbf{21}_y$ and the switch 26. The delay times of the delay elements $\mathbf{21}_1$ through $\mathbf{21}_y$ are thereby set such that the emission of the ultrasound pulse ensues in a first direction. This procedure is multiply repeated, for example, 256 times, however, the image-generating circuit 24 modifies the delay times such in every repetition of this procedure so that different emission directions of the ultrasound pulses are produced such that the sector-shaped body slice is ultimately fully scanned. Using the electrical signals obtained in this way, the image-generating circuit 24 generates, for example, a B-mode ultrasound image in a known way. In locating mode, the described execution is repeated anew, with the result that an updated ultrasound image is produced.

A joystick 29 is connected to the image-generating circuit 24, making it possible to displace a mark F' mixed into the ultrasound image displayed on the monitor 28. A focusing control 30 that is likewise connected to the joystick 29 then sets the individual delay times of the delay elements $\mathbf{22}_1$ through $\mathbf{22}_z$ via a line bust 31 so that the therapeutic ultrasound waves emanating from all regions of the ultrasound transducer elements $\mathbf{11}_1$ through $\mathbf{11}_z$ driven with an oscillator 32 are focused onto an action zone, when the switches $S1_1$ through $S1_z$, $S2_1$ through $S2_z$, $S3_1$ through $S3_z$ and $S4_1$ through $S4_z$ are placed into their position corresponding to the therapy mode. The center F of the action zone lies in the body of the subject to be treated at the location that corresponds to the location marked in the ultrasound image with the mark F'.

The therapeutic ultrasound waves are continuous sound or pulsed continuous sound. The therapeutic ultrasound waves are briefly interrupted periodically in therapy mode—which, moreover, can be turned on by actuation of the key 33, for example by the attending physician—in order to also update the ultrasound image during the therapy mode. To this end, the image-generating circuit 24 operates on the drive unit 20 and places the switches $S1_1$ through $S1_z$, $S2_1$ through S2, $S3_1$ through $S3_z$ and $S4_1$ through $S4_z$ into the position corresponding to the locating mode for the time required for generating an ultrasound image. After this, the switches return into their switch position corresponding to the therapy mode until the preparation of the next ultrasound image. Whereas the ultrasound images are generated in locating mode with a repetition rate of, for example, 25 Hz, the repetition rate in therapy mode lies, for example, at 0.2 through 1 Hz.

In therapy mode, the oscillator 32 controls the ultrasound transducers $\mathbf{8}_1$ through $\mathbf{8}_z$ to emit therapeutic ultrasound waves with a first frequency $f_1$=1–3 MHZ that is lower than the frequency $f_2$=3–9 MHZ of the diagnostic ultrasound waves that the ultrasound transduces $\mathbf{8}_1$ through $\mathbf{8}_z$ emit drive by the oscillator 27 in the locating mode. A high spatial resolution is thus advantageously achieved in the production of the ultrasound images, so that it is possible to locate the zone to be treated with enhanced precision and to position the action zone with enhanced precision in the zone to be treated.

It is generally of importance that, as already mentioned and explained, the ultrasound transducer elements $\mathbf{11}_1$ through $\mathbf{11}_z$ are respectively matched, or can be respectively matched, acoustically to the propagation medium in therapy mode as well as in diagnostics mode.

The drive circuit in FIG. 6 is to be considered only as an example. Other drive circuits that have generally the same functional scope are conceivable.

Figure 1:
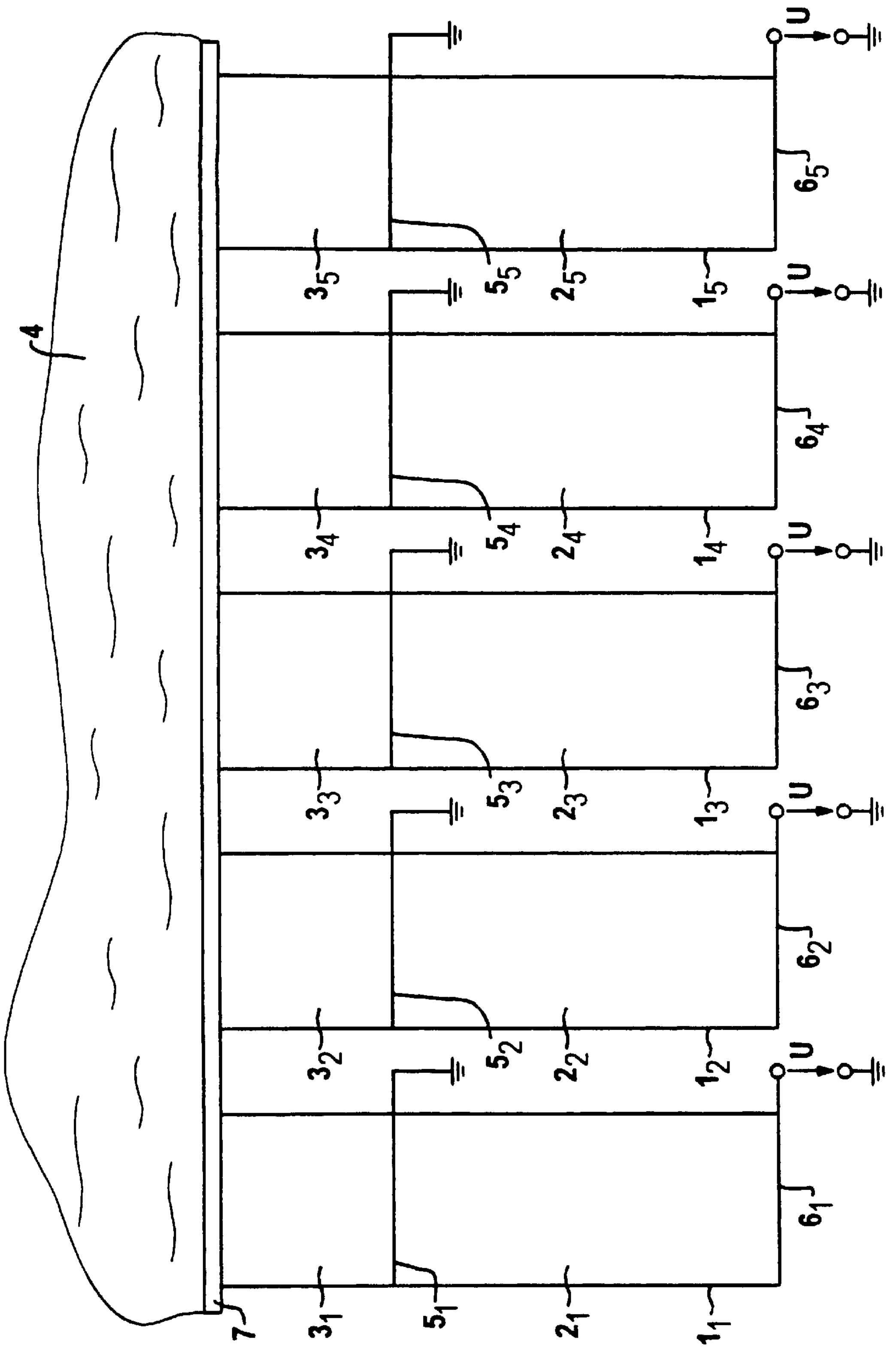
FIG.1 (PRIOR ART)
FIG. 1 is a schematic illustration of a linear phased array of ultrasound transducers having a conventional structure.
Figure 7:
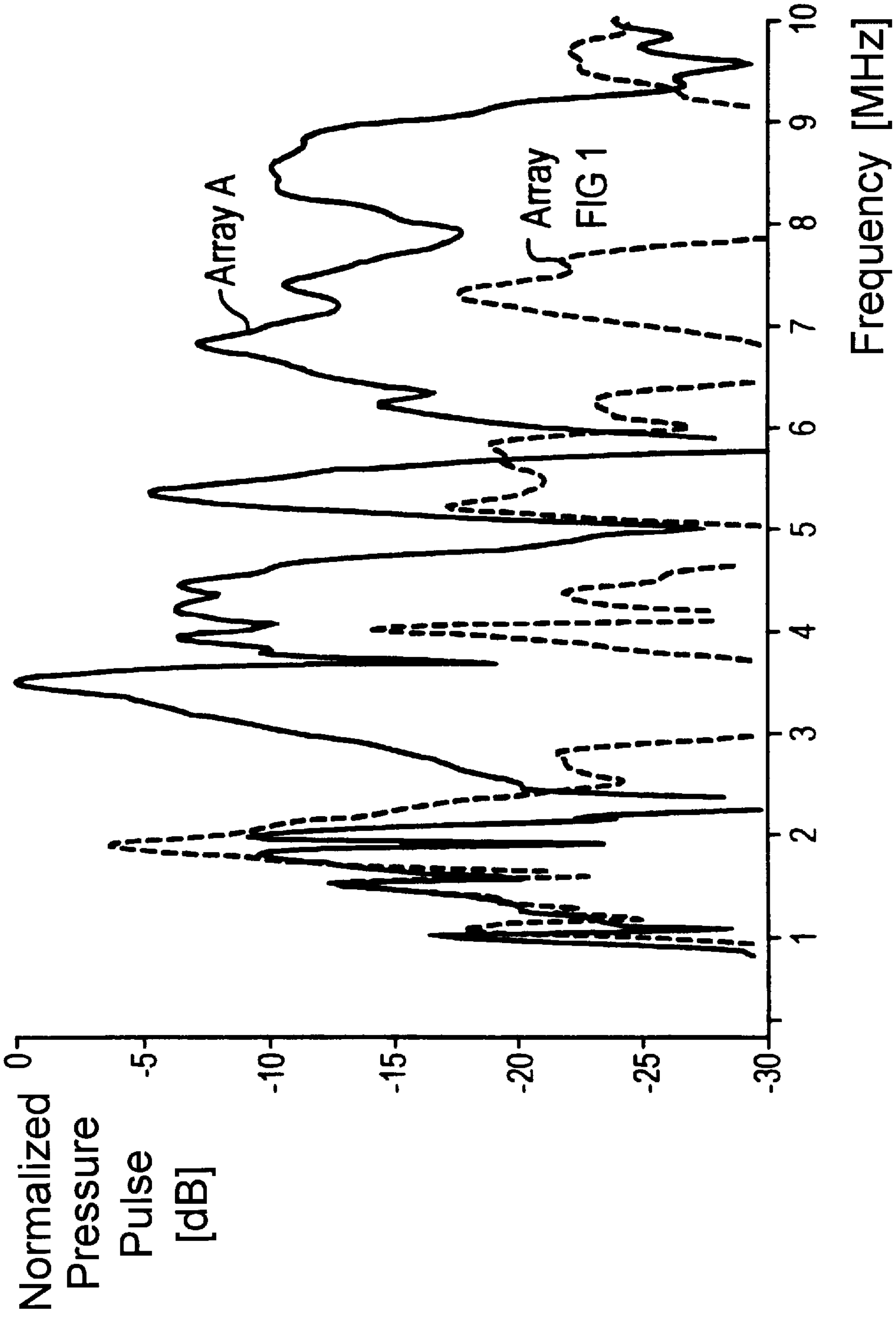
FIG. 7 shows, for comparison, ultrasound pressure pulse spectra determined by two-dimensional finite element simulation of conventional and inventive transducers.

FIG. 7 compares two ultrasound pressure pulse spectra of the ultrasound arrays of FIG. 1 and FIG. 2 determined by finite element simulation, with the simulated measurement ensuing at a distance of approximately 4 cm from the foil 7 or 17. As is clear from the illustrated pressure pulse spectra, the ultrasound array of the inventive ultrasound transducer has a significantly broader frequency spectrum and exhibits high pressure amplitudes compared to the known array shown in FIG. 1. Due to its acoustic properties, particularly the acoustic matching to the propagation medium in therapy mode and in diagnostics mode, thus, the inventive ultrasound array is very well-suited for a combined therapeutic and diagnostic mode for treating pathological tissue conditions in subjects.

Although modifications and changes may be suggested by those skilled in the art, it is the intention of the inventors to embody within the patent warranted hereon all changes and modifications as reasonably and properly come within the scope of their contribution to the art.

We claim as our invention:

1. An ultrasound transducer arrangement for diagnostic and therapeutic use for selectively generating ultrasound waves of different wavelengths respectively in a diagnostics mode and in a therapy mode, comprising:

an ultrasound transducer structure which emits ultrasound at different wavelengths in a diagnostics mode and in a therapy mode, the wavelength of the ultrasound in the diagnostics mode being shorter than the wavelength of the ultrasound in the therapy mode;

an n×λ/4 matching layer adjoining said ultrasound transducer structure for matching said transducer structure to a propagation medium, n being an odd number and λ being the wavelength of the ultrasound emitted by said ultrasound transducer structure;

said ultrasound transducer structure comprising a piezoelectric ultrasound transducer element, a first electrode for said piezoelectric ultrasound element disposed between said matching layer and said piezoelectric ultrasound transducer element, a second electrode for said piezoelectric ultrasound transducer element disposed at a side of said piezoelectric ultrasound transducer element opposite said matching layer, and a third electrode dividing said piezoelectric ultrasound transducer element into a first region disposed at a first side of said third electrode, between said matching layer and said third electrode, and into second region disposed at a second, opposite side of said third electrode, said third electrode comprising a common ground contact for said first and second regions; and control means connected to said first, second and third electrodes for applying respectively different electrical control signals across said first and second regions respectively in a diagnostics mode and in a therapy mode, said matching layer comprising means for matching the respective wavelengths of the ultrasound in the diagnostics mode and in the therapy mode.

2. An ultrasound transducer arrangement as claimed in claim 1 wherein said third electrode divides said piezoelectric ultrasound transducer element into said first and second regions in a ratio of 1:2.

3. An ultrasound transducer arrangement as claimed in claim 2 wherein said control means comprises means for applying control signals across both of said first and second regions of said piezoelectric ultrasound transducer element in the therapy mode, said control signals in combination comprising a control voltage $U_1$, and wherein said control means comprises means for applying a control voltage across said first region when said first and second regions have substantially the same polarization, which is substantially $-\frac{1}{2} U_1$, and for applying a control voltage across said first region when said first and second regions have substantially opposite polarization, which is $+\frac{1}{2} U_1$.

4. An ultrasound transducer arrangement as claimed in claim 1 wherein said control means comprises means, in said diagnostic mode, for applying a control voltage only across said first region, said first region then exhibiting an impedance, and said ultrasound transducer arrangement further comprising means for terminating said second region of said piezoelectric ultrasound transducer, in said diagnostics mode, with an electrical resistor matched to said impedance.

5. An ultrasound transducer arrangement as claimed in claim 1 wherein said first region of said piezoelectric ultrasound transducer element and said matching layer are divided into a plurality of discrete oscillators, independent of each other, and wherein said control means comprises means for supplying respectively separately control signals to said discrete oscillators.

6. An ultrasound transducer arrangement as claimed in claim 5 wherein said first region is divided into three independent discrete oscillators and wherein said control means comprises means for applying three respectively independent control voltages across said three independent discrete oscillators.

7. An ultrasound transducer arrangement as claimed in claim 6 wherein said control means comprises means for applying a control voltage $U_1$ across both of said first and second regions, and wherein said three independent control voltages comprise control voltages $U_2$, $U_3$ and $U_4$, and wherein, in said therapy mode, said control means comprises means, when said first and second regions have the same polarization, for applying control voltages $U_2=U_3=U_4=-\frac{1}{2} U_1$, and when said first and second regions have substantially opposite polarization, for applying $U_2=U_3=U_4=+\frac{1}{2} U_1$.

8. An ultrasound transducer arrangement as claimed in claim 6 wherein said control means comprises means for applying said independent control voltages only across said independent discrete oscillators in said diagnostics mode.

9. An ultrasound transducer arrangement as claimed in claim 1 wherein said ultrasound transducer structure is terminated with air at a side of said said piezoelectric ultrasound transducer element opposite said matching layer.

10. An ultrasound transducer arrangement as claimed in claim 1 wherein said piezoelectric ultrasound transducer element comprises a piezoceramic material.

11. An ultrasound transducer arrangement as claimed in claim 1 wherein said matching layer comprises a layer of epoxy resin laced with copper particles.

12. An ultrasound transducer arrangement as claimed in claim 1 wherein said piezoelectric ultrasound transducer element comprises two piezoceramic elements respectively forming said first and second regions, each piezoceramic element having a contact surface, and the respective contact surfaces of said piezoceramic elements being disposed adjacent each other and forming said third electrode.

13. An ultrasound transducer arrangement as claimed in claim 1 wherein said piezoelectric ultrasound transducer element comprises a sintered piezoceramic element produced in a sintering process, with said third electrode being formed in said sintered element during said sintering process.

14. An ultrasound transducer arrangement as claimed in claim 1 wherein said matching layer and said first region are divided into a plurality of discrete oscillators by saw kerfs.

15. An ultrasound transducer arrangement as claimed in claim 1 comprising means for focusing said ultrasound in said diagnostics mode and in said therapy mode.

16. An ultrasound transducer arrangement as claimed in claim 1 wherein said ultrasound transducer structure comprises an ultrasound array containing a plurality of ultrasound transducer elements having a structure identical to said piezoelectric ultrasound transducer element.

17. An ultrasound transducer arrangement as claimed in claim 16 wherein said control means comprises means for operating said array as a linear array.

18. An ultrasound transducer arrangement as claimed in claim 16 wherein said control means comprises means for operating said array as a phased array.

19. An ultrasound transducer arrangement as claimed in claim 16 wherein said control means comprises means for selectively operating said array as a linear array or a phased array.

20. An ultrasound transducer arrangement as claimed in claim 1 wherein said first regions and said matching region are divided into a plurality of independent discrete oscillators, and further comprising, for each discrete oscillator, a foil disposed between said matching layer and said propagation medium.

* * * * *